United States Patent
Conti et al.

(10) Patent No.: US 10,888,527 B2
(45) Date of Patent: Jan. 12, 2021

(54) STABLE SOLID PHARMACEUTICAL FORMULATIONS CONTAINING 2-(2-NITRO-4-TRIFLUOROMETHYLBENZOYL)-1,3-CYLCOHEXANEDIONE

(71) Applicant: Dipharma S.A., Chiasso (CH)

(72) Inventors: Chiara Conti, Vigolo Marchese (IT); Salvatore Agostino Giammillari, Rozzano (IT); Giuseppe Maccari, Voghera (IT)

(73) Assignee: DIPHARMA S.A., Chiasso (CH)

( * ) Notice: Subject to any disclaimer, the term of this patent is extended or adjusted under 35 U.S.C. 154(b) by 352 days.

(21) Appl. No.: 15/766,665

(22) PCT Filed: Feb. 9, 2017

(86) PCT No.: PCT/EP2017/052805
§ 371 (c)(1),
(2) Date: Apr. 6, 2018

(87) PCT Pub. No.: WO2017/137468
PCT Pub. Date: Aug. 17, 2017

(65) Prior Publication Data
US 2019/0160014 A1  May 30, 2019

(30) Foreign Application Priority Data

Feb. 11, 2016 (IT) ................ UB2016A0650

(51) Int. Cl.
*A61K 31/135* (2006.01)
*A61K 9/48* (2006.01)
*A61K 31/122* (2006.01)

(52) U.S. Cl.
CPC .......... *A61K 9/4866* (2013.01); *A61K 9/4825* (2013.01); *A61K 9/4858* (2013.01); *A61K 31/122* (2013.01)

(58) Field of Classification Search
CPC .................................... A61K 31/135
USPC ........................................... 514/646
See application file for complete search history.

(56) References Cited

U.S. PATENT DOCUMENTS

| | | |
|---|---|---|
| 5,550,165 A | 8/1996 | Ellis et al. |
| 8,354,451 B2 | 1/2013 | Moran et al. |

FOREIGN PATENT DOCUMENTS

| | | |
|---|---|---|
| EP | 0591275 B1 | 3/1999 |
| EP | 1853241 B1 | 9/2011 |
| WO | WO 2010/054273 A1 | 5/2010 |
| WO | WO 2011/106655 A1 | 9/2011 |
| WO | WO 2012/177214 A1 | 12/2012 |
| WO | WO 2013/181292 A1 | 12/2013 |
| WO | WO 2015/101794 A1 | 7/2015 |

OTHER PUBLICATIONS

Lock et al., "The Role of Nitisinone in Tyrosine Pathway Disorders," *Curr Rheumatol Rep 16*:457, Springer Science+Business Media, New York (2014).

Introne et al., "A 3-year Randomized Therapeutic Trial of Nitisinone in Alkaptonuria," *Mol Genet Metab 103*(4):307-314, Elsevier Inc. (2011).

*Primary Examiner* — Raymond J Henley, III
(74) *Attorney, Agent, or Firm* — Sterne, Kessler, Goldstein & Fox P.L.L.C.

(57) ABSTRACT

The present invention relates to highly stable drug dosage forms comprising. The invention also contemplates said highly stable drug dosage forms for the treatment of diseases where inhibition of 4-hydroxyphenylpyruvate dioxygenase 5 will result at improving the health of the patient.

20 Claims, 8 Drawing Sheets

STABLE SOLID PHARMACEUTICAL FORMULATIONS CONTAINING 2-(2-NITRO-4-TRIFLUOROMETHYLBENZOYL)-1,3-CYLCOHEXANEDIONE

FIELD OF THE INVENTION

The present invention relates to highly stable drug dosage forms comprising a compound susceptible to degradation, notably temperature-induced, and at least one pharmaceutically acceptable excipient.

More specifically, the invention regards the 4-hydroxyphenylpyruvate dioxygenase (HPPD) inhibitor 2-(2-nitro-4-trifluoromethylbenzoyl)-1,3-cyclohexanedione, also known as nitisinone or NTBC.

BACKGROUND OF THE INVENTION

NTBC is a drug marketed by Swedish Orphan Biovitrum International AB under the brand name Orfadin® and it is used to slow the effects of hereditary tyrosinemia type 1 (HT-1) in adult and pediatric patients. It has been approved by FDA and EMA in January 2002 and February 2005 respectively.

HT-1 disease is due to a deficiency of the final enzyme of the tyrosine catabolic pathway fumarylacetoacetate hydrolase. NTBC is a competitive inhibitor of 4-hydroxyphenylpyruvate dioxygenase (HPPD), an enzyme which precedes fumarylacetoacetate hydrolase. By inhibiting the normal catabolism of tyrosine in patients with HT-1, NTBC prevents the accumulation of the toxic intermediates maleylacetoacetate and fumarylacetoacetate, that in patients with HT-1 are converted to the toxic metabolites succinylacetone and succinylacetoacetate, the former inhibiting the porphyrin synthesis pathway leading to the accumulation of 5-aminolevulinate.

Usefulness of NTBC in the treatment of further diseases has also been documented. A non-comprehensive list is reported hereinafter.

WO2011106655 reports a method for increasing tyrosine plasma concentrations in a subject suffering from oculocutaneous/ocular albinism, the method comprising administering to the subject a pharmaceutically acceptable composition comprising NTBC in the range of between about 0.1 mg/kg/day to about 10 mg/kg/day.

U.S. Pat. No. 8,354,451B2 reports new methods of combating microbial infections due to fungi or bacteria by means of administration to a subject of a therapeutically active amount of NTBC.

WO2010054273 discloses NTBC-containing compositions and methods for the treatment and/or prevention of restless leg syndrome (RLS).

EP1853241B1 claims the use of NTBC in the treatment of a neurodegenerative disease, notably Parkinson disease.

Introne W. J., et al., disclosed usefulness of nitisinone in the treatment of alkaptonuria (Introne W. J., et al., Molec. Genet. Metab., 2011, 103, 4, 307).

It is well known that one of the problems of the actual drug formulation (i.e., Orfadin® capsules) is its chemical stability. Indeed, even if Orfadin® has to be stored in a refrigerator at a temperature ranging from 2° C. to 8° C., its shelf life is of only 18 months. After first opening, the in-use stability is a single period of 2 months at a temperature not above 25° C., after which it must be discarded. It will be evident that such storage conditions have an impact in the distribution chain of the medicine, in terms of costs and also in terms of logistics for the patient. Therefore, there is an urgent need of more stable formulations, both from a logistic supply chain point of view, and from the patient compliance point of view.

Usefulness of Orfadin® in the treatment of diseases where the products of the action of HPPD are involved (e.g., HT-1) has been described notably in EP0591275B1. Synthesis of NTBC is also described in this patent. Among suitable pharmaceutical formulations described herein, the Applicants mentioned various conventional compositions such as tablets, lozenges, hard or soft capsules, aqueous or oily suspensions, emulsions, dispersible powders or granules, syrups or elixirs. Parenteral formulations (for example sterile aqueous or oily solution for intravenous, subcutaneous, intramuscular or intravascular dosing), or rectal formulations such as a suppository are also disclosed. EP0591275B1 reported 3 specific examples of formulations, two of which being tablets and one in the form of capsules. The latter dosage forms contained 2% of active ingredient, 0.3% of a lubricant (i.e., magnesium stearate) the rest being lactose Ph.Eur present as a diluent. Those capsules were then used for in-vivo studies.

WO2015101794 filed in name of Cycle Pharmaceuticals LTD reports tablet formulation of NTBC, said formulation allegedly conferring greater stability with respect to that of Orfadin® capsule formulation. The Applicants also referred that one of the major drawbacks of the currently available commercial product resides in thermic stability issues, notably by forming an undesired cyclized product named 6-trifluoromethyl-3,4-dihydro-2H-xanthene-1,9-dione or oxotetrahydroxanthone. The Applicant further identified lubricant magnesium stearate (not present in Orfadin® capsule formulation) as an accelerating factor of instability of NTBC. The application further suggested not to use any metal ion or any starch in the formulation. In particular, the Applicant disclosed that starch promotes the formation of the unwanted cyclized impurities oxotetrahydroxanthone. This patent application also suggested tablet formulation as the preferred one. As a lubricant, fatty acids containing from 20 to 22 carbon atoms were preferred, more preferably the fat of the composition consists of glycerol dibehenate (e.g., Compritol® 888). It was suggested that this component in association with lactose may even enhance the stability of the formulation, preventing formation of the undesired cyclized product.

WO2012177214 filed in name of Swedish Orphan Biovitrum International AB discloses oral liquid suspensions of nitisinone containing citric acid buffer as a stabilizer.

WO2013181292 filed in name of Biotie Therapies Inc., and now abandoned, disclosed pharmaceutical formulations of nitisinone which were alleged to be stabilized for long term storage. Among a long list of hypothetical stabilizers, the Applicants suggest dicarboxylic and tricarboxylic acids as the particularly preferred organic acids, those being selected from the group consisting of citric, pyruvic, succinic, fumaric, malic, oxaloacetic, cis-aconitic, isocitric, and α-ketoglutaric acids. Stability studies of a tablet formulation obtained from a wet granulation process to enable uniform distribution of the various ingredients have been performed under accelerated conditions. The Applicants suggested that the presence of citric acid enabled stabilization of the formulation.

However, to date, notwithstanding numerous efforts, no NTBC formulation fully satisfies the requisites of stability and/or compliance standard for the patients. Therefore, there is an unmet medical need of long-term stable formulations.

DESCRIPTION OF THE INVENTION

The present invention relates to a highly and durably stable pharmaceutical composition comprising 2-(2-nitro-4- trifluoromethylbenzoyl)-1,3-cyclohexanedione as the active ingredient, one stabilizer and at least one excipient.

While not intending to be bound in any way by theory, it is believed that the improved stability of the formulation is due to the presence of stearic acid.

We have now found that formulating nitisinone with stearic acid as a stabilizer, surprisingly gives rise to highly stable pharmaceutical compositions even at room temperature for long period of time.

In a preferred embodiment, such formulation comprises pregelatinized starch or lactose as excipient or a mixture thereof.

In a more preferred embodiment, such formulation is in the form of hard gelatin capsules.

If usefulness of stearic acid as a lubricant in drug formulation has been known for long, its use as a stabilizer of nitisinone has never been mentioned or suggested. Moreover, contrarily to what suggested in the prior art, starch as a diluent is not incompatible to the integrity of nitisinone if stearic acid is also present in the pharmaceutical composition.

In one preferred embodiment of the present invention, pregelatinized starch is used as a diluent, and stearic acid as a stabilizer.

In another preferred embodiment of the present invention, lactose is used as a diluent, and stearic acid as a stabilizer.

In a further preferred embodiment of the present invention, a mixture of lactose and pregelatinized starch is used as a diluent, and stearic acid as a stabilizer. In such a formulation, the ratio pregelatinized starch/lactose preferably ranges from 5/95 to 95/5.

In a still preferred embodiment of the present invention, percentage of each ingredient w/w is as follows: from 2 to 5%, from 93 to 97% and from 0.5 to 5%, such percentages relating to nitisinone, diluent (i.e., pregelatinized starch or lactose) and stearic acid respectively.

In a more preferred embodiment of the present invention, stearic acid is present at a concentration of up to 1% w/w±10%.

In a still more preferred embodiment of the present invention, percentage of each ingredient w/w is as follows: 3.57%, 95.34% and 1.09%, such percentages relating to nitisinone, diluent (i.e., pregelatinized starch or lactose) and stearic acid respectively.

In an even more preferred embodiment of the present invention, the pharmaceutical formulations object of the present invention can be in four different strengths with regard to the amount of the active ingredient nitisinone, said strengths being 2 mg, 5 mg, 10 mg and 20 mg.

The pharmaceutical formulation of the present invention is useful as a medicament due to its 4-hydroxyphenylpyruvate dioxygenase inhibiting properties for the treatment of disorders where such inhibition results in improving the health of the patient. In particular, patients suffering from HT-1, or from oculocutaneous/ocular albinism, or from microbial infections due to fungi or bacteria, or from restless leg syndrome, or from neurodegenerative disease, notably Parkinson disease can be treated.

In a preferred embodiment of the present invention, the pharmaceutical formulation is for treating patients suffering from HT-1.

Generally, the pharmaceutical formulation of the present invention is administered in a "therapeutically effective amount". The amount of the pharmaceutical formulation actually administered will typically be determined by a physician, in the light of the relevant circumstances, including the condition to be treated, any other potential drug the patient is currently taking, the age, the sex, body weight, and response of the individual patient, the severity of the patient's symptoms, and the like.

Generally, an effective dose will be from 0.5 mg/kg/day to 2 mg/kg/day, preferably 1 mg/kg/day to 1.5 mg/kg/day. Such a daily dose may be divided in two equal doses, and taken twice a day at about the same time each day.

In a preferred embodiment, the daily dose is divided in two equal doses.

Dose adjustment will be made according to level monitoring of urine succinylacetone and alpha-fetoproteins, and liver function test values.

It will be appreciated that HT-1 patients are under a restricted tyrosine and phenylalanine diet, meanwhile under treatment with the pharmaceutical formulation of the present invention.

The expression "% w/w" refers to the percentage of a substance present in the pharmaceutical formulation on a weight by weight basis (i.e., 1 g/100 g is equivalent to 1% w/w).

The expression "about the same time" means ±30 min prior or after the usual administration time.

The expressions "highly stable" and/or "durably stable" mean that the chemical integrity of the active ingredient is of at least 95% after one month of storage of the drug dosage form at 25° C. and 60% RH.

In one embodiment, said chemical integrity is of at least 96% after one month of storage of the drug dosage form at 25° C. and 60% RH.

In another embodiment, said chemical integrity is of at least 97% after one month of storage of the drug dosage form at 25° C. and 60% RH.

In a preferred embodiment, said chemical integrity is of at least 98% after one month of storage of the drug dosage form at 25° C. and 60% RH.

In a still preferred embodiment, said chemical integrity is of at least 99% after one month of storage of the drug dosage form at 25° C. and 60% RH.

Another embodiment of the invention contemplates chemical integrity of the drug dosage form after three months of storage at 25° C. and 60% RH.

In said embodiment, the chemical integrity of the drug dosage form is of at least 95% after three months of storage of the drug dosage form at 25° C. and 60% RH.

In a preferred embodiment, the chemical integrity of the drug dosage form is of at least 96% after three months of storage of the drug dosage form at 25° C. and 60% RH.

In another preferred embodiment, the chemical integrity of the drug dosage form is of at least 97% after three months of storage of the drug dosage form at 25° C. and 60% RH.

In a still preferred embodiment, the chemical integrity of the drug dosage form is of at least 98% after three months of storage of the drug dosage form at 25° C. and 60% RH.

In a still more preferred embodiment, the chemical integrity of the drug dosage form is of at least 99% after three months of storage of the drug dosage form at 25° C. and 60% RH.

Another embodiment of the invention contemplates chemical integrity of the drug dosage form after one month of storage at 40° C. and 75% RH.

In said embodiment, the chemical integrity of the drug dosage form is of at least 95% after one month of storage of the drug dosage form at 40° C. and 75% RH.

In a preferred embodiment, the chemical integrity of the drug dosage form is of at least 96% after one month of storage of the drug dosage form at 40° C. and 75% RH.

In another preferred embodiment, the chemical integrity of the drug dosage form is of at least 97% after one month of storage of the drug dosage form at 40° C. and 75% RH.

In a still preferred embodiment, the chemical integrity of the drug dosage form is of at least 98% after one month of storage of the drug dosage form at 40° C. and 75% RH.

In a still more preferred embodiment, the chemical integrity of the drug dosage form is of at least 99% after one month of storage of the drug dosage form at 40° C. and 75% RH.

Another embodiment of the invention contemplates chemical integrity of the drug dosage form after three months of storage at 40° C. and 75% RH.

In said embodiment, the chemical integrity of the drug dosage form is of at least 95% after three months of storage of the drug dosage form at 40° C. and 75% RH.

In a preferred embodiment, the chemical integrity of the drug dosage form is of at least 96% after three months of storage of the drug dosage form at 40° C. and 75% RH.

In another preferred embodiment, the chemical integrity of the drug dosage form is of at least 97% after three months of storage of the drug dosage form at 40° C. and 75% RH.

In a still preferred embodiment, the chemical integrity of the drug dosage form is of at least 98% after three months of storage of the drug dosage form at 40° C. and 75% RH.

In a still more preferred embodiment, the chemical integrity of the drug dosage form is of at least 99% after three months of storage of the drug dosage form at 40° C. and 75% RH.

3 impurities were detected under stressed storage conditions and have been chemically characterized as being 4-(trifluoromethyl)salicylic acid, 6-trifluoromethyl-3,4-dihydro-2H-xanthene-1,9-dione, and 1,3-cyclohexanedione. They are further referred to as Imp-1, Imp-2, and Imp-3. Such impurities had been previously reported in WO2015101794.

It is submitted that testing at 40° C. and 75% RH for a short time such as six months, is considered indicative of stability at 25° C. (i.e., room temperature) for a longer period of time (fifteen to eighteen months).

EXAMPLES

Figure 1A:
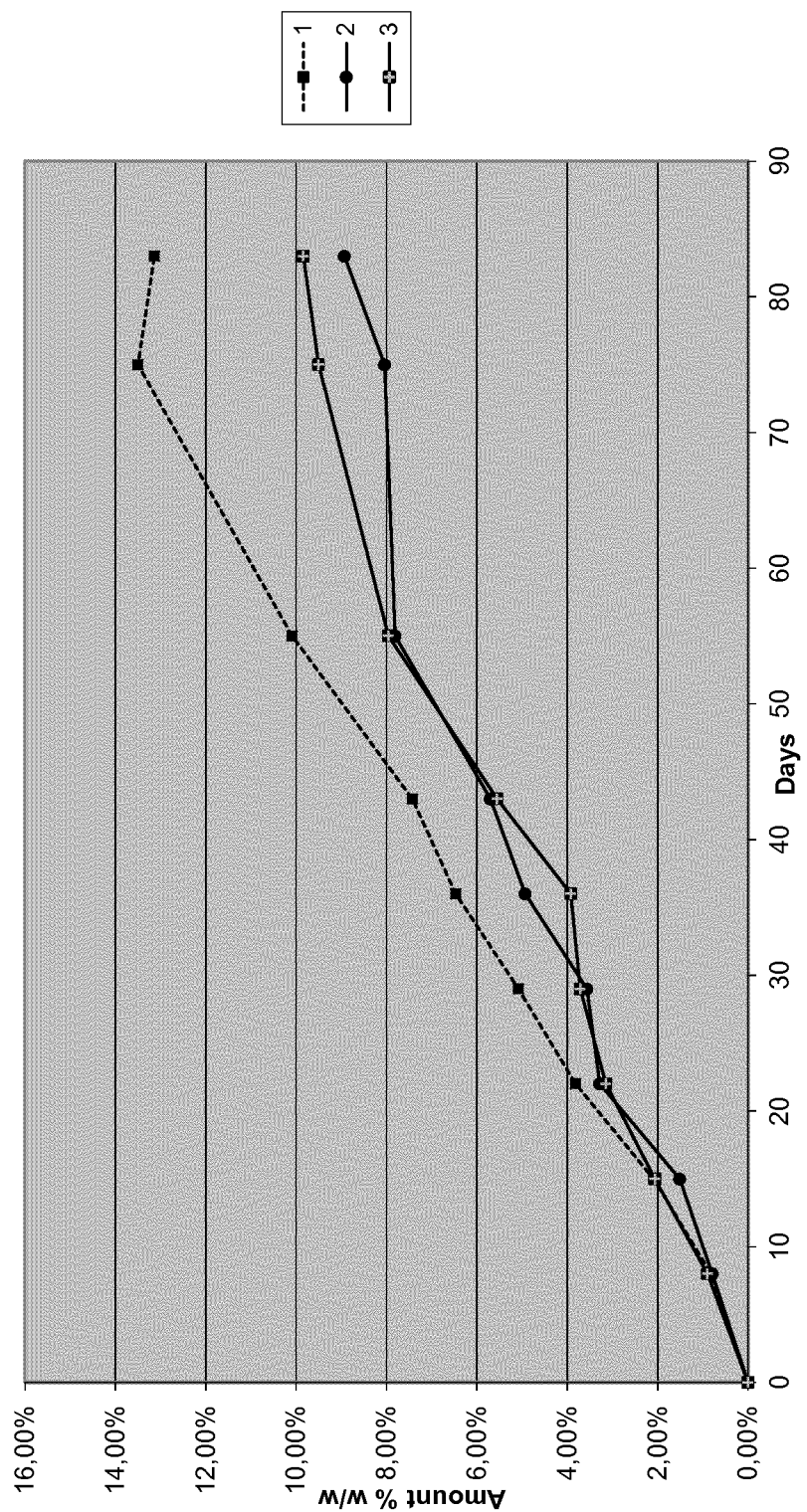
FIG. 1A: amount of Imp-2 from feasibility examples 1 to 3 over a 3 month period in accelerated stability conditions.
Figure 1B:
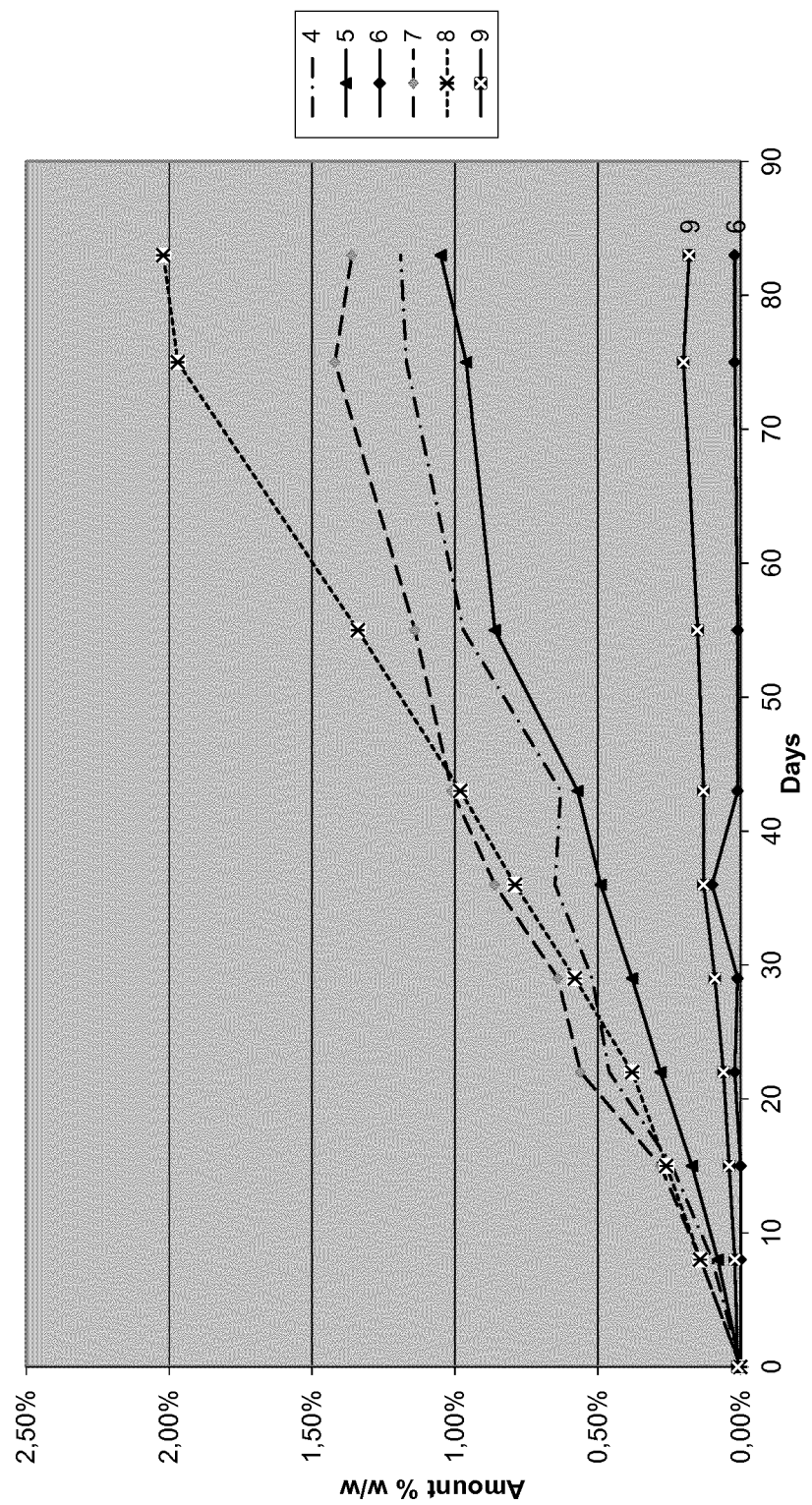
FIG. 1B: amount of Imp-2 from feasibility examples 4 to 9 over a 3 month period in accelerated stability conditions.
Figure 2A:
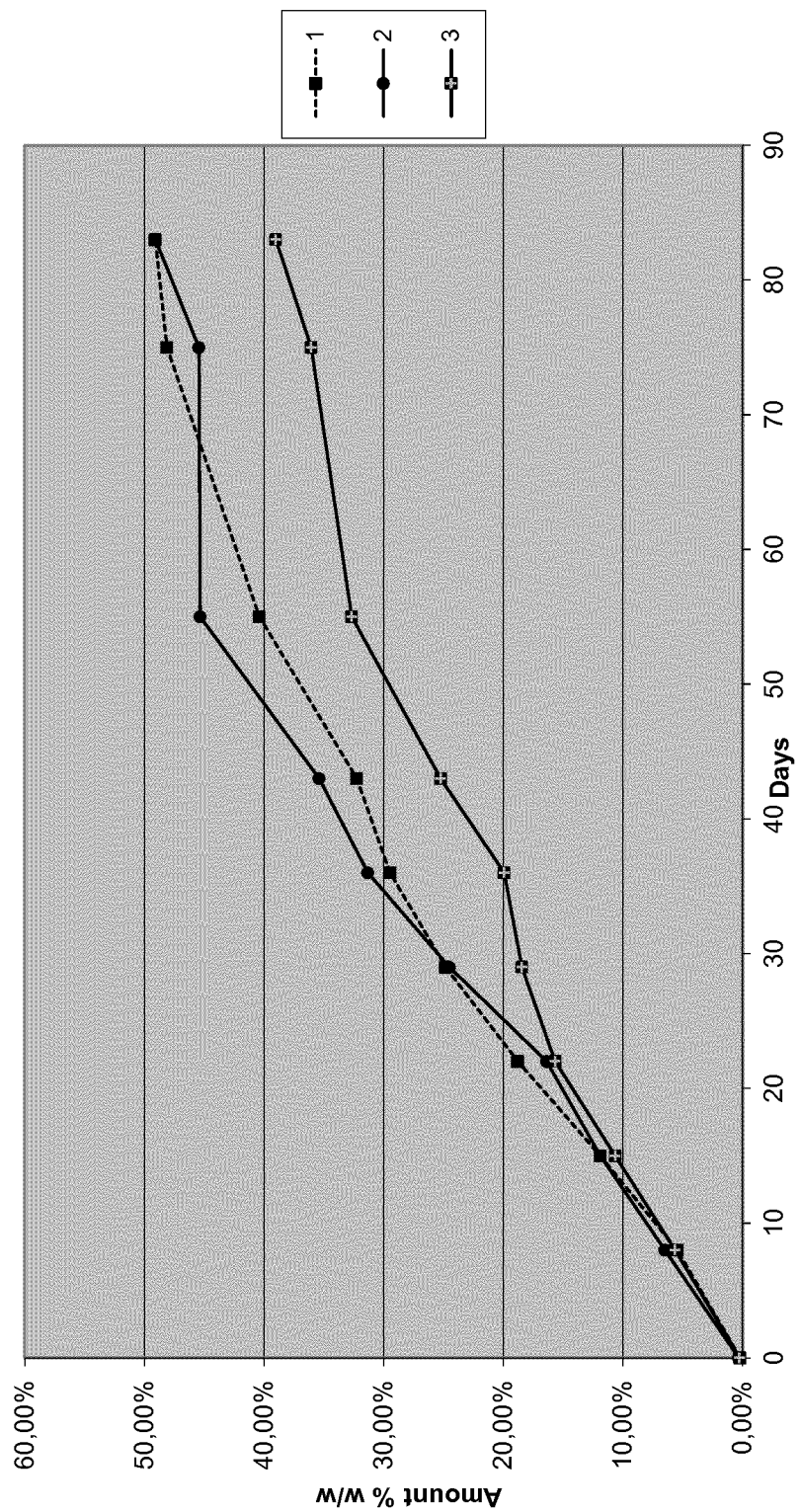
FIG. 2A: amount of total impurities from feasibility examples 1 to 3 over a 3 month period in accelerated stability conditions.
Figure 2B:
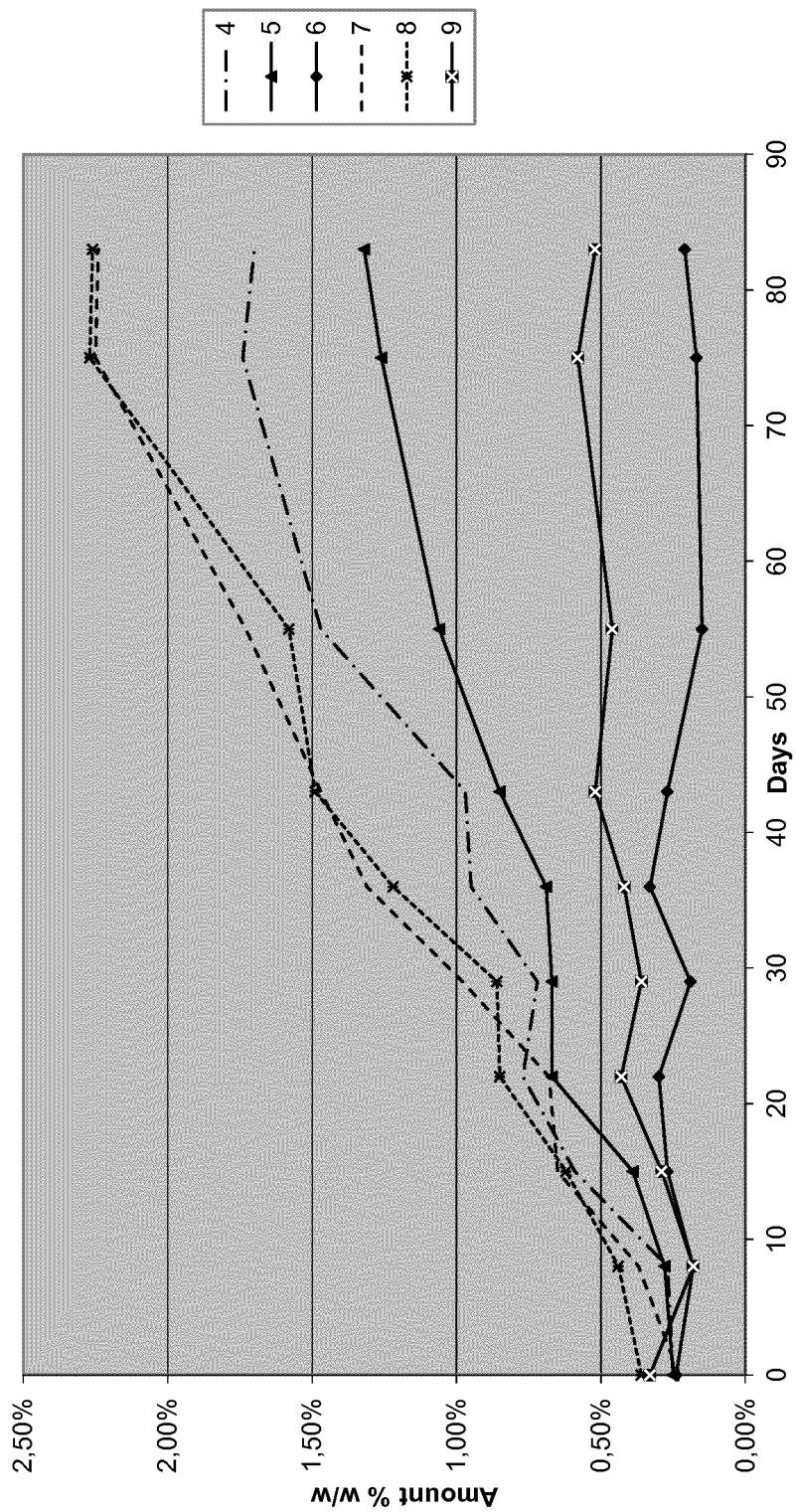
FIG. 2B: amount of total impurities from feasibility examples 4 to 9 over a 3 month period in accelerated stability conditions.
Figure 3A:
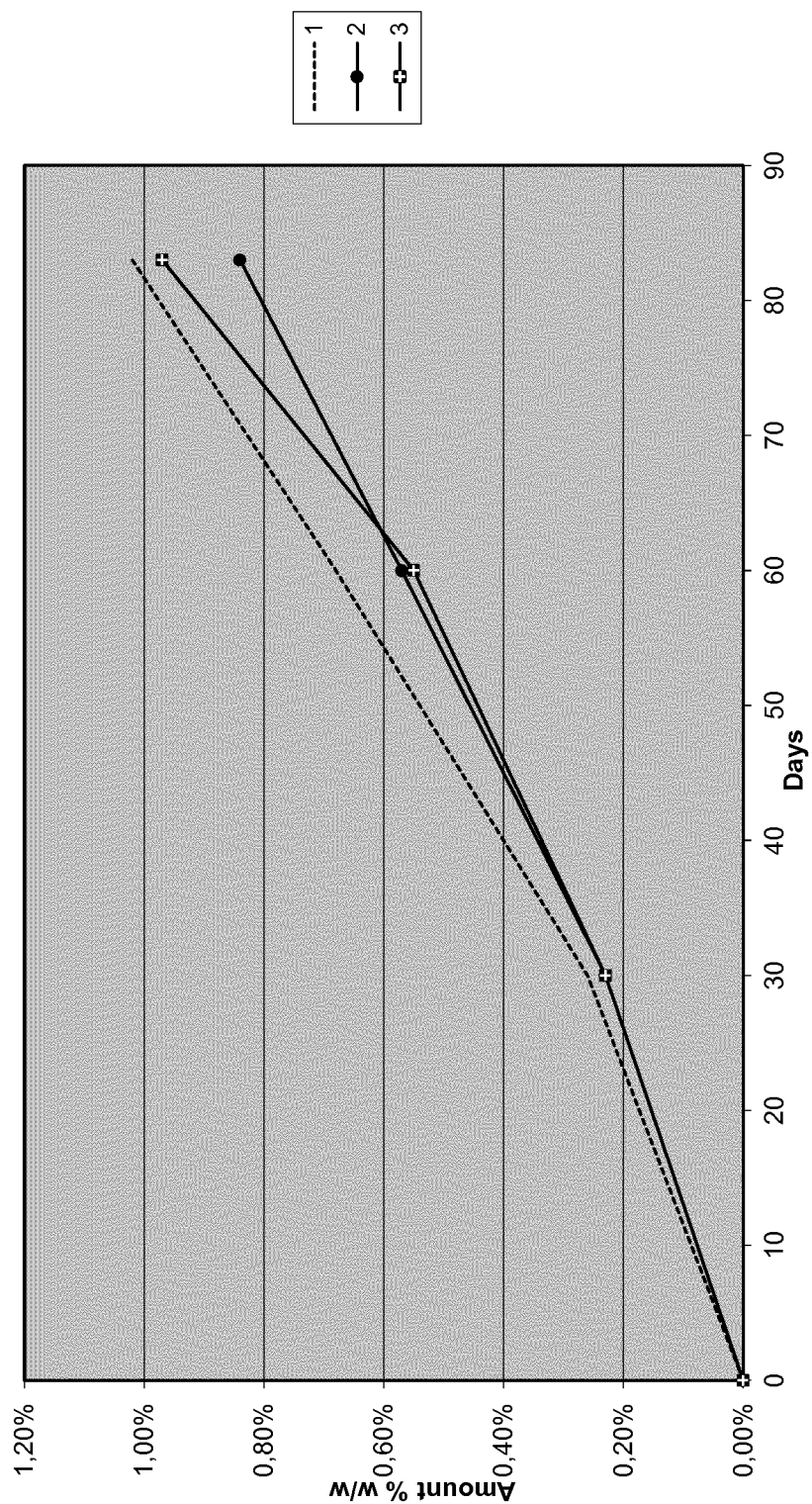
FIG. 3A: amount of Imp-2 from feasibility examples 1 to 3 over a 3 month period in long-term stability conditions.
Figure 3B:
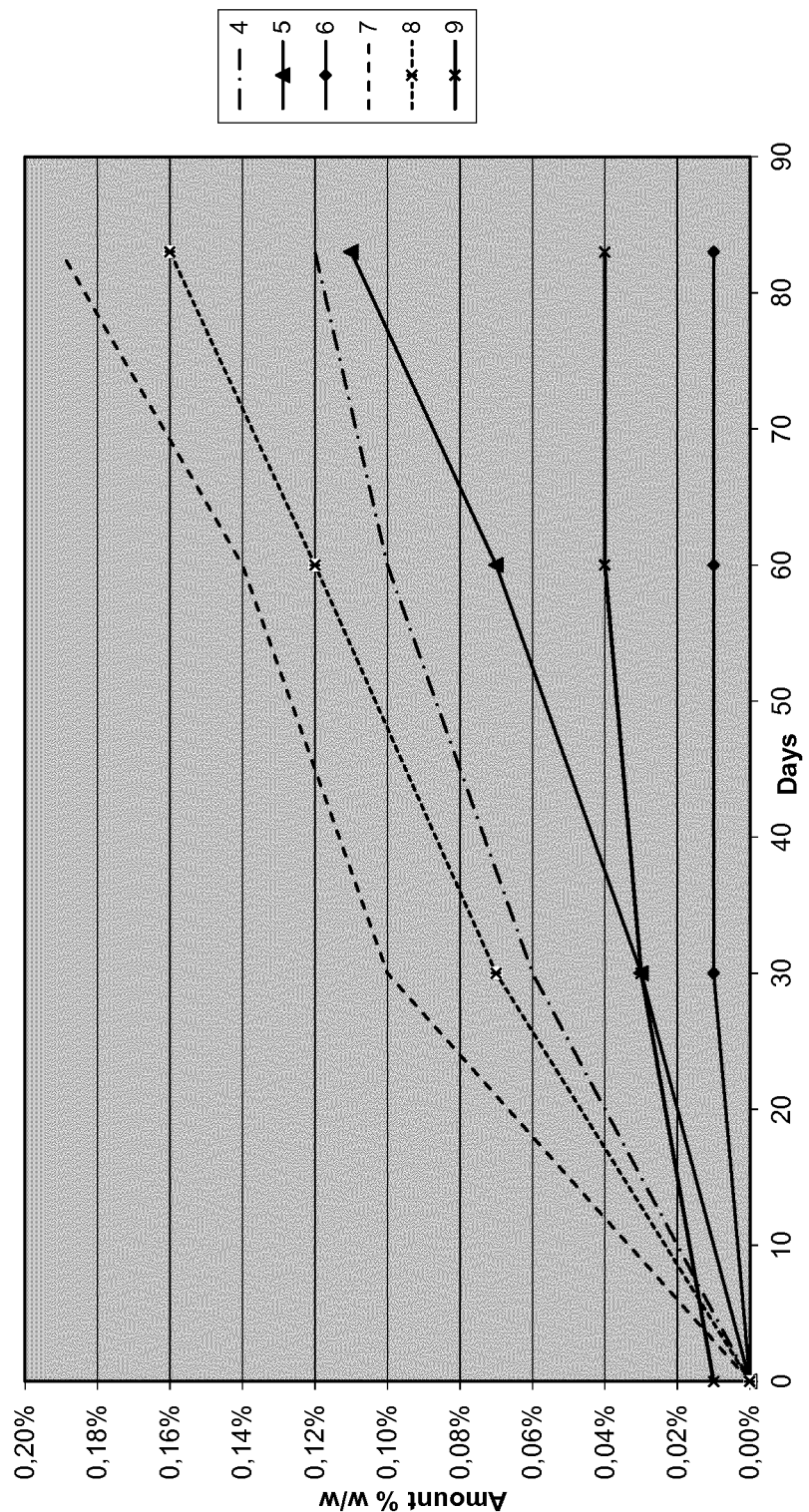
FIG. 3B: amount of Imp-2 from feasibility examples 4 to 9 over a 3 month period in long-term stability conditions.

Nine pharmaceutical formulations, as disclosed in Table 1, were tested as reported in feasibility examples 1-9.

TABLE 1

| Ingredients | Feasibility examples | | | | | | | | |
|---|---|---|---|---|---|---|---|---|---|
| | 1 | 2 | 3 | 4 | 5 | 6 | 7 | 8 | 9 |
| Nitisinone | X | X | X | X | X | X | X | X | X |
| $HPO_4^{2-}$ $Ca^{2+}$ | X | X | X | | | | | | |
| Pregelatinized starch | | | | | | | X | X | X |
| Lactose monohydrate | | | | X | X | X | | | |
| Mg stearate | X | | | X | | | X | | |
| Stearic acid | | | X | | | X | | | X |
| None | | X | | | X | | | X | |

Material Used:

Active Pharmaceutical Ingredient

Nitisinone was obtained following the procedure described in EP0805791B1. Its chemical purity (i.e., 99.95%) was assessed by means of HPLC at a wavelength detection of 235 nm.

Diluent

Pregelatinized starch: (Starch 1500®; Colorcon, Eighenmann & Veronelli)

Lactose monohydrate: (Lactopress® spray dried; DFE Pharma)

Dibasic calcium phosphate anhydrous (DI-CAFOS®, Budenheim)

Lubricant

Stearic acid (Stearic acid 50, Carlo Erba)

Magnesium stearate (vegetal grade, Ligamed MF-3-V, Peter Greven Nederland)

FEASIBILITY EXAMPLES

Pharmaceutical Formulations

General protocol to obtain the exemplified feasibility pharmaceutical formulations is described herein underneath.

Nitisinone (2.5 mg) and diluent (269.75 mg) were mixed in Turbula® at 23 rpm for 3 minutes. The lubricant (2.75 mg) was then added, and the mixing was continued for another minute at the same mixing velocity (i.e., 23 rpm). In cases where no lubricant was added, the amount of diluent was adjusted to 272.5 mg, and the mixing step length adjusted to 4 minutes.

Hard gelatin capsules size 2 were then filled by means of a semi-automatic Zuma OSZ/150 filling machine with 275 mg of mixture containing 2.5 mg of nitisinone, 1% w/w of lubricant (if present), the rest being the diluent material.

Storage Conditions

Capsules were stored at three different atmospheric conditions (i.e., temperature and Relative Humidity (RH)) as reported underneath.

Condition 1 (refrigerated stability study) 5° C./

Condition 2 (long-term stability study) 25° C./60% RH

Condition 3 (accelerated stability study) 40° C./75% RH

Appropriate analytical methods were developed to fully assess the impurity profile of the pharmaceutical formulations at various time points as reported underneath.

The pharmaceutical formulations of the feasibility examples were obtained using the general protocol reported herein above, selecting the appropriate ingredients. During the feasibility studies, total amount of impurities was considered, and results are depicted in FIGS. 1A, 1B, 2A, 2B, 3A, 3B, 4A and 4B.

Analytical Methods

Dissolution phase (DP): $CH_3CN/H_2O$: 1/1

Column: Sunfire C18 5 µm, 250×4.6 mm

Flow: 1 ml/min

Injection volume: 10 µl

Detector wavelength: 235 nm
Column temperature: 35° C.
Elution conditions for impurities 1 and 2 (i.e., Imp-1 and Imp-2)
Eluent A: $CH_3CN$
Eluent B: $CH_3CO_2NH_4$ 0.02M
Gradient-1:

| Time | % A | % B |
|------|-----|-----|
| 0    | 15  | 85  |
| 25   | 75  | 25  |
| 35   | 75  | 25  |
| 36   | 15  | 85  |

Run time: 35 mn, post-time: 11 min
Elution conditions for impurity 3 (i.e., Imp-3)
Eluent C: $CH_3CN$
Eluent D: $H_3PO_4$ 0.1%
Gradient-2:

| Time | % C | % D |
|------|-----|-----|
| 0    | 10  | 90  |
| 15   | 85  | 15  |
| 25   | 85  | 15  |
| 26   | 10  | 90  |

Figure 4A:
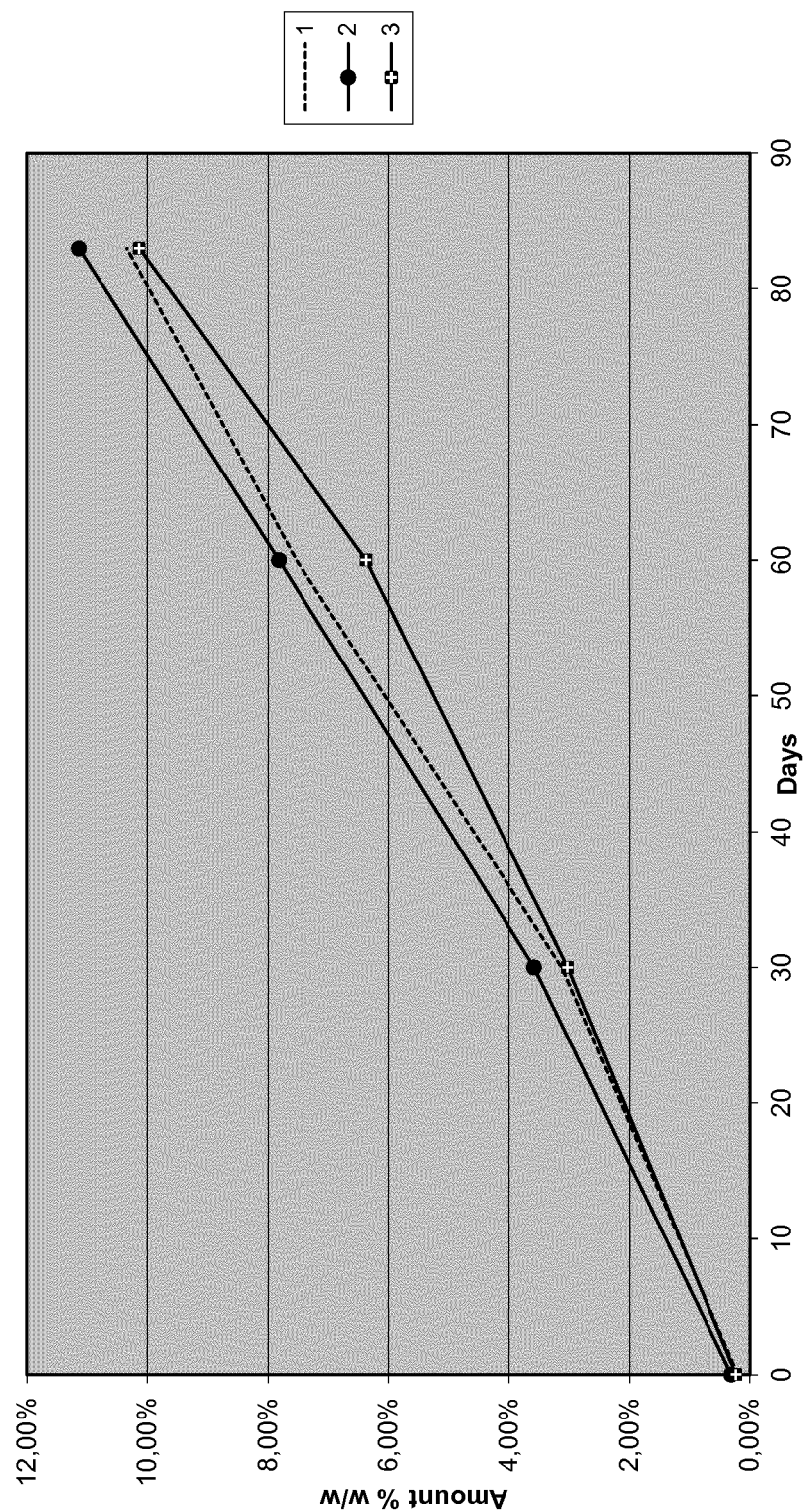
FIG. 4A: amount of total impurities from feasibility examples 1 to 3 over a 3 month period in long-term stability conditions.
Figure 4B:
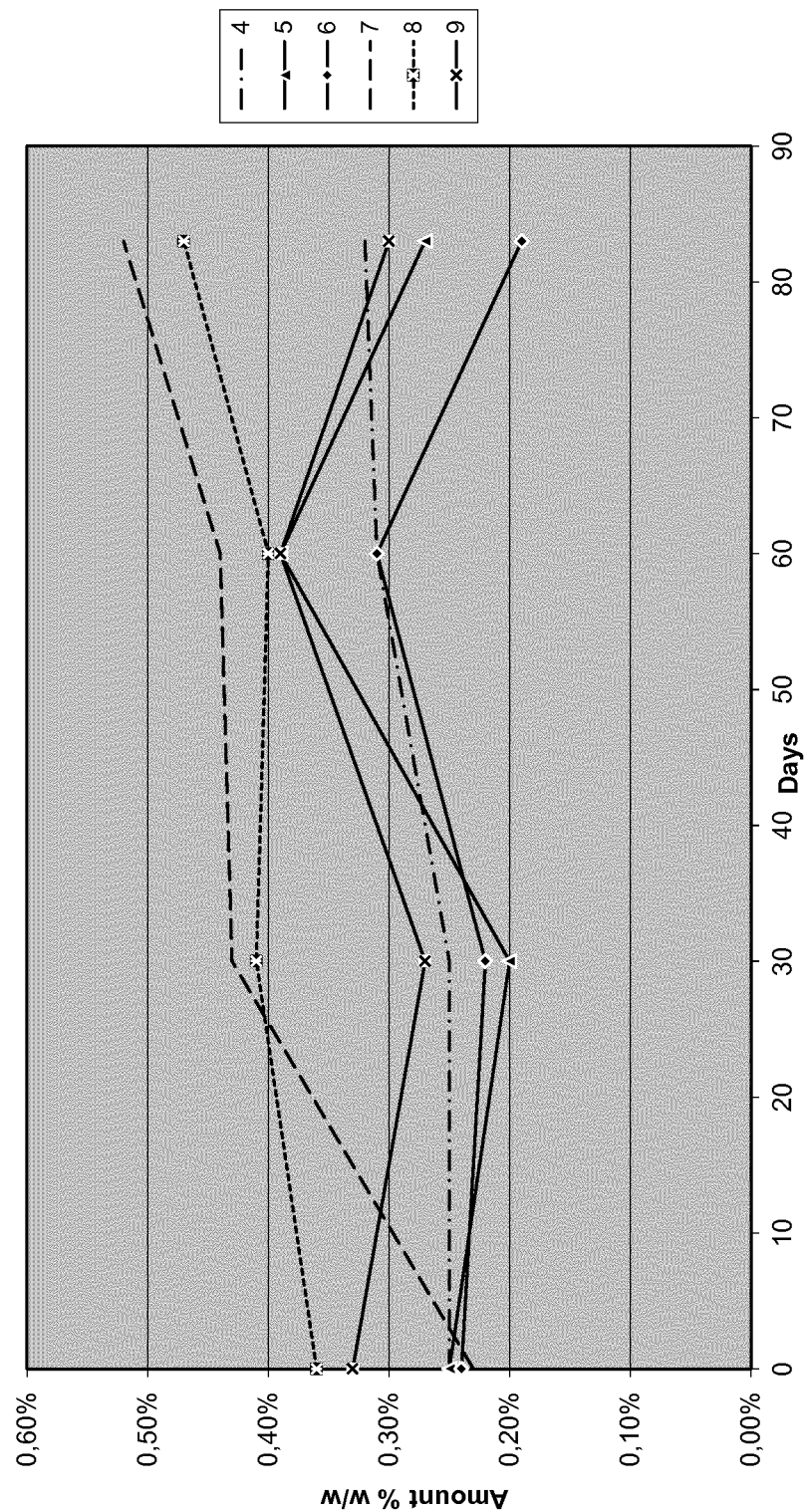
FIG. 4B: amount of total impurities from feasibility examples 4 to 9 over a 3 month period in long-term stability conditions.

Run time: 25 min, post-time: 1 min
Dissolution Method
Test Solution 50 mg of formulated nitisinone to be analyzed are dissolved in 2 ml of $CH_3CN$ in a 50 ml volumetric flask. Said solution is then adjusted to 50 ml by addition of required amount of DP.
Reference Solution A
10 mg of nitisinone (reference standard) and 15 mg of each Imp-1 and Imp-2 are dissolved in 2 ml of $CH_3CN$ in a 100 ml volumetric flask. Said solution is then adjusted to 100 ml by addition of required amount of DP. One ml of the thus obtained solution is then diluted up to 100 ml with 99 ml of DP.
The reference solution contains 0.10% of nitisinone and 0.15% of each of the impurities.
Reference Solution B
15 mg of Imp-3 are dissolved in a 100 ml volumetric flask with DP up to 100 ml. One ml of the thus obtained solution is then diluted up to 100 ml with 99 ml of DP.
The reference solution contains 0.15% of Imp-3.
Formulations containing calcium phosphate dibasic as a diluent (i.e., feasibility examples 1-3) resulted unstable, since rapidly allowing formation of the cyclized impurity even after one month, either at 40° C./75% RH or also at 25° C./60% RH, even if in a lower extent. This is highlighted in FIGS. 1A and 3A respectively.
It is interesting to note that calcium phosphate dibasic-containing formulations are less prone to formation of cyclized degradation product if no lubricant is present, stearic acid demonstrating even a negative effect with regard to formation of oxotetrahydroxanthone (i.e., FIG. 1A). When looking for any impurities forming during storage conditions, it is evident that none of the formulations of feasibility examples 1-3 are suitable since after 3 months around 40 to 50% of impurities are formed at 40° C./75% RH (i.e., FIG. 2A), meanwhile more that 10% of nitisinone is degraded after 3 months at 25° C./60% RH (FIG. 4A).

Formulation containing lactose (i.e., feasibility examples 4-6) resulted extremely stable when also comprising stearic acid. Magnesium stearate had a negative influence when considering formation of oxotetrahydroxanthone both in accelerated and long term stabilities studies (i.e., FIGS. 1B and 3B respectively). This trend can also be observed when considering all impurities formed during storage, whatever the conditions used (i.e., FIGS. 2B and 4B). Surprisingly, presence of stearic acid hugely improved stability of nitisinone/lactose formulation (feasibility example 6 versus feasibility examples 4 and 5 in tables 1B, 2B, 3B and 4B).

Formulations containing pregelatinized starch (i.e., feasibility examples 7-9) resulted extremely stable when also comprising stearic acid, the formation of oxotetrahydroxanthone being very limited. Indeed, surprisingly, the amount of oxotetrahydroxanthone was reduced by more than 11 folds in accelerated stability experiments (feasibility example 6 versus feasibility example 5, FIG. 1B). The level of any other impurities also remained at an extremely low level even in accelerated stability conditions (i.e., 0.34% after 3 months at 40° C./75% RH).

Starting from promising formulations of feasibility examples 6 and 9, additional experiments were conducted to identify formulations with further improved stability profile. Chemical compositions illustrated in examples 1-3, derived from feasibility example 9, showed an extremely high stability profile.

EXAMPLES 1-3

| Role | Ingredients | Examples | | |
|------|-------------|---|---|---|
|      |             | 1 | 2 | 3 |
| API | Nitisinone (mg) | 10 | 5 | 2 |
| Diluent | Pregelatinized starch (mg) | 266.95 | 133.47 | 53.39 |
| Lubricant | Stearic acid (mg) | 3.05 | 1.53 | 0.61 |

Mixing
For large scale batch, nitisinone is placed in a low-density polyethylene (LDPE) bag together with 25% of the total amount of the diluent and mixed for 1 min at 10 rpm to get "premix 1". Thereafter, another 25% of the total amount of the diluent is added to "premix 1" and mixed again in the same conditions as previously to get "premix 2". The latter is then transferred into a biconic mixer together with the remaining 50% of the total amount of the diluent and stearic acid is then added. The whole mixture is then mixed for 10 min±2 min.

Capsules Filling
Capsules size 2 (for the 10 mg strength capsules and size 3 for the 2 and 5 mg strength capsules) were filled using an automatic IN-CAP filling machine (Bonapace).

Dissolution Test
Such test was performed in a vessel containing 900 ml of a pH 6.8 buffer made of $KH_2PO_4$ and NaOH in deionized water.

Stability
Stability of 10 mg strength capsules (i.e., example 1) was analyzed in order to fully assess the impurities profile of the pharmaceutical formulation at various time points. The analytical method used is reported underneath.

Analytical Method
Dissolution phase (DP): CH$_3$CN/MeOH:65/35
Column: Phenomenex Synergi 4 μm™ Hydro-RP 80A 100×4.6 mm
Flow: 1.5 ml/min
Injection volume: 10 μl
Detector wavelength: 255 nm and 310 nm
Column temperature: 30° C.
Eluent A: CH$_3$CN
Eluent B: Acetate buffer solution pH 3
Gradient:

| Time | % A | % B |
|---|---|---|
| 0 | 5 | 95 |
| 10 | 23 | 77 |
| 25 | 70 | 30 |
| 45 | 70 | 30 |
| 50 | 5 | 95 |
| 60 | 5 | 95 |

TABLE 2

Refrigerated stability study (5° C.)

| | Time (qty %) | | | |
|---|---|---|---|---|
| Assay | Time 0 | Month 1 | Month 3 | Month 6 |
| Dissolution at 45 min | 99$^a$ | 99$^a$ | 102$^a$ | 93$^b$ |
| Nitisinone | 101.1 | 101.1 | 101.6 | 96.7 |
| Impurity 1 | ND | ND | ND | ND |
| Impurity 2 | <0.05 | <0.05 | <0.05 | <0.05 |
| Impurity 3 | ND | ND | ND | ND |

$^a$75 rpm;
$^b$50 rpm;
ND: not detected

TABLE 3

Long-term stability study (25° C./60% RH)

| | Time (qty %) | | | |
|---|---|---|---|---|
| Assay | Time 0 | Month 1 | Month 3 | Month 6 |
| Dissolution at 45 min | 99$^a$ | NT | NT | NT |
| Nitisinone | 101.1 | 103.4 | 102.1 | 95.7 |
| Impurity 1 | ND | ND | ND | ND |
| Impurity 2 | <0.05 | <0.05 | <0.05 | <0.05 |
| Impurity 3 | ND | ND | ND | ND |

$^a$75 rpm;
$^b$50 rpm;
ND: not detected;
NT: not tested

TABLE 4

Accelerated stability study (40° C./75% RH)

| | Time (qty %) | | | |
|---|---|---|---|---|
| Assay | Time 0 | Month 1 | Month 3 | Month 6 |
| Dissolution at 45 min | 99$^a$ | 101$^a$ | 95.2$^a$ | NT |
| Nitisinone | 101.1 | 101.7 | 101.9 | 95.2 |
| Impurity 1 | ND | ND | ND | ND |

TABLE 4-continued

Accelerated stability study (40° C./75% RH)

| | Time (qty %) | | | |
|---|---|---|---|---|
| Assay | Time 0 | Month 1 | Month 3 | Month 6 |
| Impurity 2 | <0.05 | <0.05 | <0.05 | <0.05 |
| Impurity 3 | ND | ND | ND | ND |

$^a$75 rpm;
$^b$50 rpm;
ND: not detected;
NT: not tested

As the skilled person will understand from the results reported in Tables 2 to 4, such a formulation is highly stable over time, independently from the storage conditions. Moreover, the usual impurity 6-trifluoromethyl-3,4-dihydro-2H-xanthene-1,9-dione (i.e., Imp-2) is below 0.05%.

The invention claimed is:

1. A stable solid pharmaceutical formulation comprising 2-(2-nitro-4-trifluoromethylbenzoyl)-1,3-cyclohexanedione as a pharmaceutically active ingredient, pregelatinized starch and stearic acid.

2. The stable solid pharmaceutical formulation according to claim 1, wherein the amount of stearic acid represents from 0.5 to 5% w/w of the total amount of the ingredients.

3. The stable solid pharmaceutical formulation according to claim 2, wherein the amount of stearic acid represents 1% w/w±10% of the total amount of the ingredients.

4. The stable solid pharmaceutical formulation according to claim 1, wherein the chemical integrity of 2-(2-nitro-4-trifluoromethylbenzoyl)-1,3-cyclohexanedione is of at least 95% after three months of storage at 25° C.

5. The stable solid pharmaceutical formulation according to claim 1, further comprising a 6-trifluoromethyl-3,4-dihydro-2H-xanthene-1,9-dione impurity, wherein the amount of 6-trifluoromethyl-3,4-dihydro-2H-xanthene-1,9-dione does not exceed 0.20% after three months of storage at 40° C./75% RH.

6. The stable solid pharmaceutical formulation according to claim 1 in the form of a gelatin capsule, wherein the amount of 2-(2-nitro-4-trifluoromethylbenzoyl)-1,3-cyclohexanedione is 2 mg, 5 mg, 10 mg, or 20 mg.

7. The stable solid pharmaceutical formulation according to claim 6, wherein the gelatin capsule is a hard gelatin capsule.

8. The stable solid pharmaceutical formulation according to claim 4, wherein the chemical integrity of 2-(2-nitro-4-trifluoromethylbenzoyl)-1,3-cyclohexanedione is of at least 97% after three months of storage at 25° C.

9. The stable solid pharmaceutical formulation according to claim 8, wherein the chemical integrity of 2-(2-nitro-4-trifluoromethylbenzoyl)-1,3-cyclohexanedione is of at least 98% after three months of storage at 25° C.

10. The stable solid pharmaceutical formulation according to claim 9, wherein the chemical integrity of 2-(2-nitro-4-trifluoromethylbenzoyl)-1,3-cyclohexanedione is of at least 99% after three months of storage at 25° C.

11. A method of inhibiting 4-hydroxyphenylpyruvate dioxygenase in a patient, the method comprising administering to the patient the stable solid pharmaceutical formulation according to claim 1.

12. A method of treating oculocutaneous/ocular albinism, microbial infections, restless leg syndrome, alkaptonuria, or hereditary tyrosinemia type 1 in a patient, the method comprising administering to the patient the stable solid pharmaceutical formulation according to claim 1.

13. The method according to claim 12, wherein the disease to be treated is hereditary tyrosinemia type 1.

14. A method of treating oculocutaneous/ocular albinism, microbial infections, restless leg syndrome, alkaptonuria, or hereditary tyrosinemia type 1 in a patient, the method comprising administering to the patient the stable solid pharmaceutical formulation according to claim 2.

15. A method of treating oculocutaneous/ocular albinism, microbial infections, restless leg syndrome, alkaptonuria, or hereditary tyrosinemia type 1 in a patient, the method comprising administering to the patient the stable solid pharmaceutical formulation according to claim 3.

16. A method of treating oculocutaneous/ocular albinism, microbial infections, restless leg syndrome, alkaptonuria, or hereditary tyrosinemia type 1 in a patient, the method comprising administering to the patient the solid pharmaceutical formulation according to claim 4.

17. A method of treating oculocutaneous/ocular albinism, microbial infections, restless leg syndrome, alkaptonuria, or hereditary tyrosinemia type 1 in a patient, the method comprising administering to the patient the stable solid pharmaceutical formulation according to claim 5.

18. A method of treating oculocutaneous/ocular albinism, microbial infections, restless leg syndrome, alkaptonuria, or hereditary tyrosinemia type 1 in a patient, the method comprising administering to the patient the solid pharmaceutical formulation according to claim 6.

19. A method of treating oculocutaneous/ocular albinism, microbial infections, restless leg syndrome, alkaptonuria, or hereditary tyrosinemia type 1 in a patient, the method comprising administering to the patient the stable solid pharmaceutical formulation according to claim 7.

20. A method of treating oculocutaneous/ocular albinism, microbial infections, restless leg syndrome, alkaptonuria, or hereditary tyrosinemia type 1 in a patient, the method comprising administering to the patient the stable solid pharmaceutical formulation according to claim 8.

* * * * *